United States Patent [19]

Sternberg

[11] 4,268,171
[45] May 19, 1981

[54] METHOD DETERMINING CONCENTRATION IN RATE NEPHELOMETRIC IMMUNOCHEMICAL ANALYSIS

[75] Inventor: James C. Sternberg, Fullerton, Calif.

[73] Assignee: Beckman Instruments, Inc., Fullerton, Calif.

[21] Appl. No.: 38,978

[22] Filed: May 14, 1979

Related U.S. Application Data

[63] Continuation of Ser. No. 816,414, Jul. 18, 1977, abandoned.

[51] Int. Cl.³ .......................................... G01N 21/00
[52] U.S. Cl. .............................. 356/341; 23/230 B; 356/338
[58] Field of Search ............... 356/103, 104, 201, 204, 356/341, 338; 23/230 B

[56] References Cited

U.S. PATENT DOCUMENTS

| | | | |
|---|---|---|---|
| 3,725,204 | 4/1973 | Marshall | 356/103 |
| 3,730,842 | 5/1973 | Wyatt | 356/103 |
| 3,748,044 | 7/1973 | Liston | 356/180 |
| 3,832,532 | 8/1974 | Praglin | 356/103 |
| 3,905,767 | 9/1975 | Morris | 356/103 |
| 3,967,901 | 7/1976 | Rodriguez | 356/103 |
| 3,990,851 | 11/1976 | Gross | 356/103 |
| 4,063,817 | 12/1977 | Shimamura | 356/180 |

OTHER PUBLICATIONS

Sternberg, "Spectrophotometric Analysis of Multi . . . ", Analytical Chemistry 32, (1960), pp. 84–90.

Primary Examiner—Donald P. Walsh
Attorney, Agent, or Firm—R. J. Steinmeyer; Robert R. Meads; Donald A. Streck

[57] ABSTRACT

A method of determining the concentration of antigen in a rate nephelometric immunochemical analysis wherein an observed maximum rate of change of a nephelometric signal is used to determine the antigen concentration by employing a mathematical expression derived on a semi-empirical basis.

1 Claim, 6 Drawing Figures

METHOD DETERMINING CONCENTRATION IN RATE NEPHELOMETRIC IMMUNOCHEMICAL ANALYSIS

This is a continuation, of application Ser. No. 816,414, filed July 18, 1977 now abandon.

BACKGROUND OF THE INVENTION

The present invention relates to immunochemical analysis techniques and more particularly to rate nephelometric immunochemical analysis.

In copending United States patent application No. 796,621, by Robert J. Anderson et al. entitled A SYSTEM FOR RATE IMMUNONEPHELOMETRIC ANALYSIS, assigned to the common assignee of this application, a system is described for antigen/antibody analysis employing rate nephelometric techniques. The rate of change with respect to time of a nephelometric signal obtained from an antibody-antigen reaction is monitored on a continuing basis. The maximum or peak rate of change of the reaction and the time to that peak rate is determined. Over a portion of a curve obtained by plotting peak rate (H) v. antigen concentration (C) for the particular reaction the curve is taken as linear so that by limiting the analysis to that falling on the "linear" portion of the curve the concentration is taken to be substantially equal to a constant times the peak rate.

Such a conclusion is, at best, true over only a very limited portion of the curve. Likewise, the amount of the curve which will behave in a linear manner is a function of the particular antigen-antibody reaction being monitored. In actuality, the curve of peak rate (H) v. antigen concentration (C) is appreciably nonlinear and cannot be fit by a conventional power series of less than fourth order, e.g., $H = a_0 + a_1 C + a_2 C^2 + a_3 C^3 + a_4 C^4 + \ldots$ Where a relationship of such complexity is involved, normal practice would be to determine the unknown antigen concentration C by plotting and then referring to a calibration curve H v. C. Such a curve would be generated by measuring peak rates obtained with a set of known dilutions of an antigen sample (calibrator) of known concentration. The set would usually include at least five different dilutions. Having generated the calibration curve, the unknown concentration of an antigen in an antibody-antigen reaction would be determined by measuring the peak rate and then reading the concentration value which corresponds to the measured peak rate on the calibration curve.

The foregoing is a tedious manual procedure. It is, therefore, desirable to obtain an approximation equation for the H v. C curve which will permit the mathematical calculation of unknown concentration values (C) within acceptable limits from measured values of peak rates (H). It is further desirable that the approximation equation be solvable for the concentration values on a real-time basis, as by iterative methods, within a reasonable time constraint, to provide maximum throughput in a clinical situation.

Therefore, it is the object of the present invention to provide a method of determining concentration from peak rate data in a rate nephelometric immunochemical analysis system employing a mathematical approximation of at least the antibody excess portion of the H v. C curve.

SUMMARY

The foregoing objective is achieved by employing a special form of cubic equation (not a conventional power series), derived on a semi-empirical basis, to calculate concentration from peak rate. The formula used is:

$$H = \frac{MEC^2(1 - AC)}{1 + (E - A)C}$$

where:

H is observed peak rate from the reaction,

C is concentration, and

M, E, and A are system and reagent related constants.

Thus, the method of the present invention comprises the steps of monitoring the rate of change with respect to time of a nephelometric signal produced by an antibody/antigen reaction to determine the peak rate (H) and then calculating the concentration (C) of antigen according to the foregoing formula.

To derive the formula, the antibody/antigen reaction was analyzed as being analogous to an electrical circuit. In this regard, the highly nonlinear H v. C curve was broken into two portions ($H_1$ and $H_2$) which could be closely matched to parabolas following known mathematical expressions. The two curve portions and the mathematical expressions therefor were considered as being analogous to two series connected electrical conductance elements for passing a "chemical current." The value of H and hence the foregoing formula was determined employing the electrical analogs for the curve portions $H_1$ and $H_2$ such that $1/H = 1/H_1 + 1/H_2$.

DESCRIPTION OF THE PREFERRED EMBODIMENT

In rate nephelometric analysis of immunochemical constituents, the extremely nonlinear nature of the peak rate v. antigen concentration (H v. C) curve creates severe problems in the accurate determination of antigen concentrations from experimentally observed nephelometric responses. Following typical practices, it would be necessary to tediously map out a multi-point calibration curve. This would be accomplished by introducing standard samples (calibrators) at several levels of known antigen concentration and measuring the peak rate response obtained. The calibration curve would then be used to indicate unknown values of antigen concentrations from observed responses by locating the observed response point on the calibration curve and then reading the concentration as the other coordinate of the point.

Figure 1:
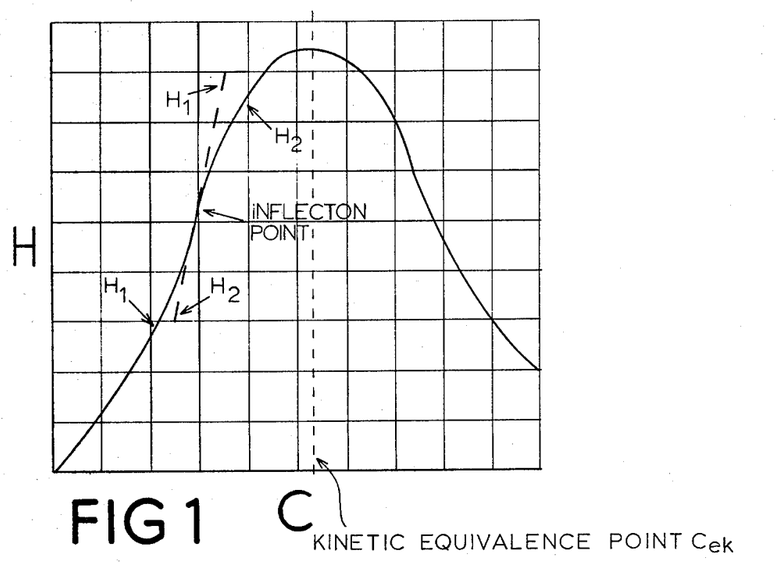
FIG. 1 is a graph of the peak rate (H) v. concentration (C) in a typical antigen/antibody reaction.
Figure 2:
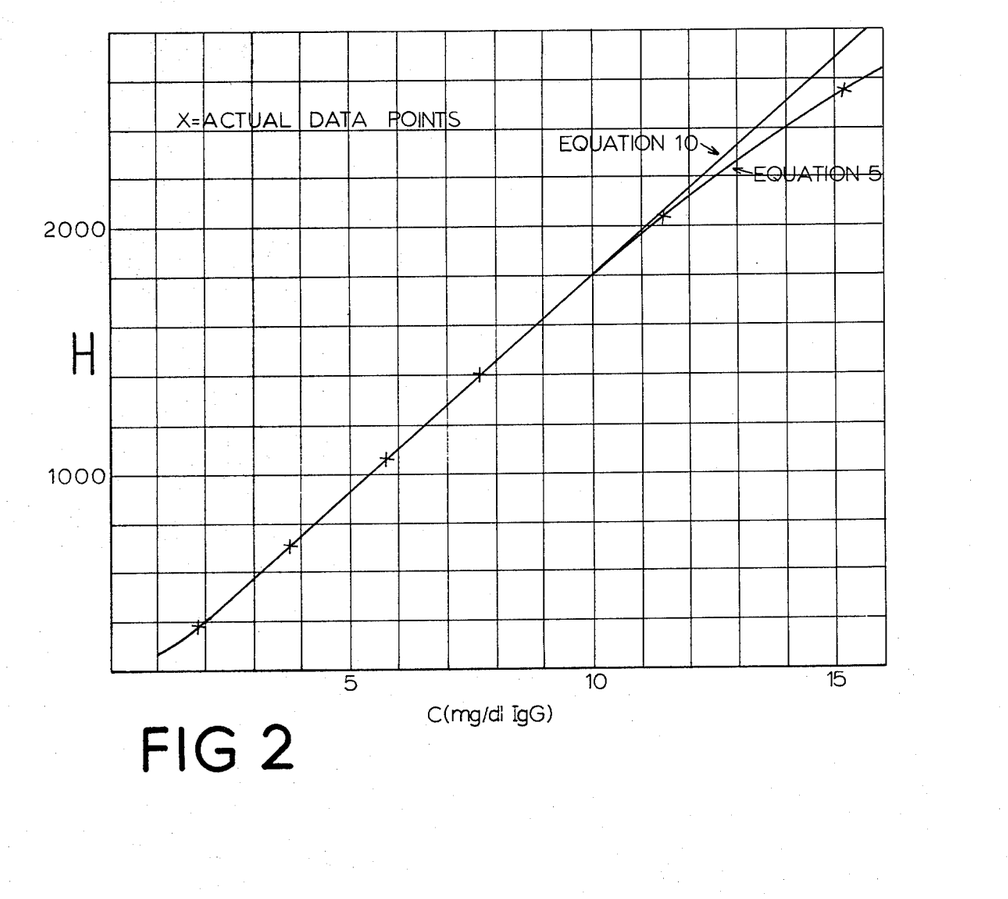
FIG. 2 is a graph of the fit of curves according to the present invention against actual data points for a human immunoglobulin G (IgG) antigen/antibody reaction.
Figure 3:
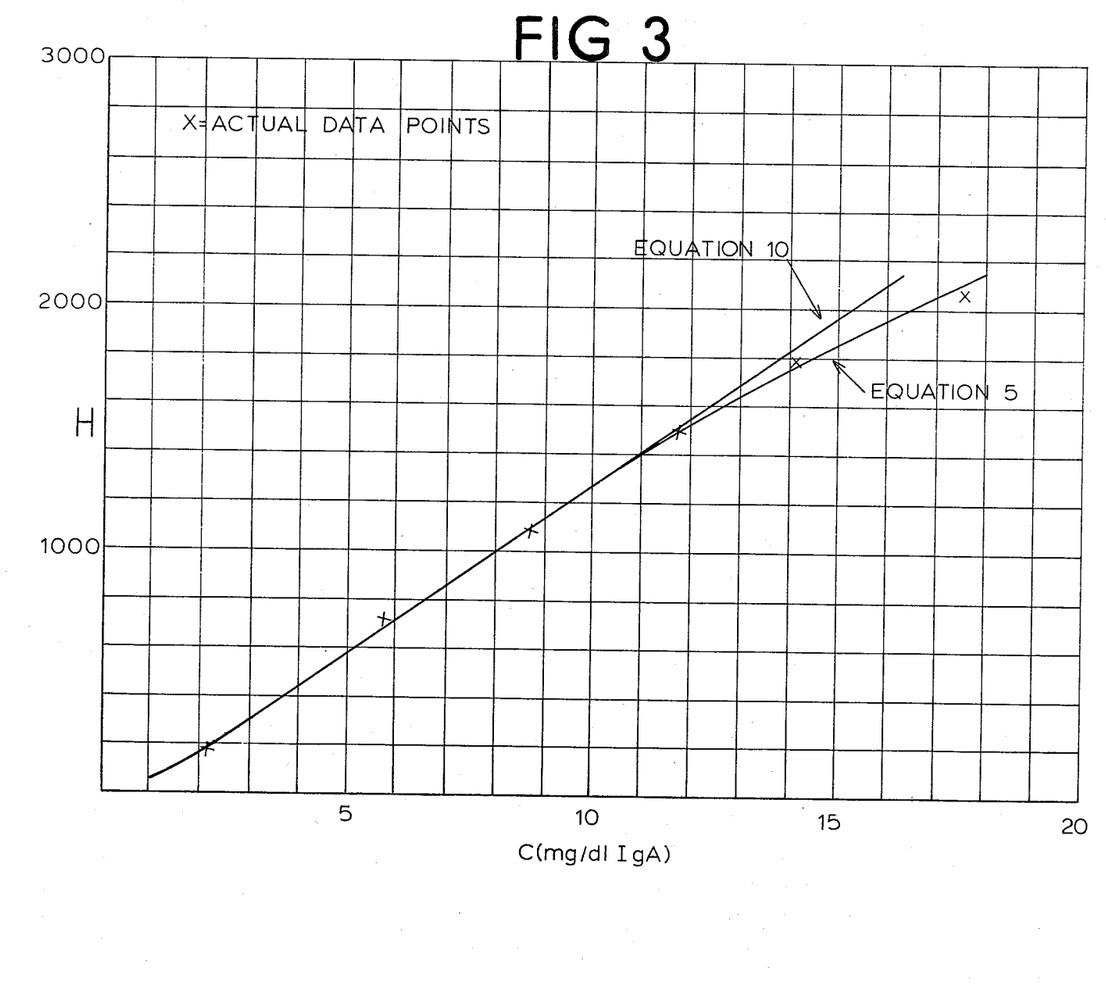
FIG. 3 is a graph of the fit of curves according to the present invention against actual data points for a human immunoglobulin A (IgA) antigen/antibody reaction.
Figure 4:
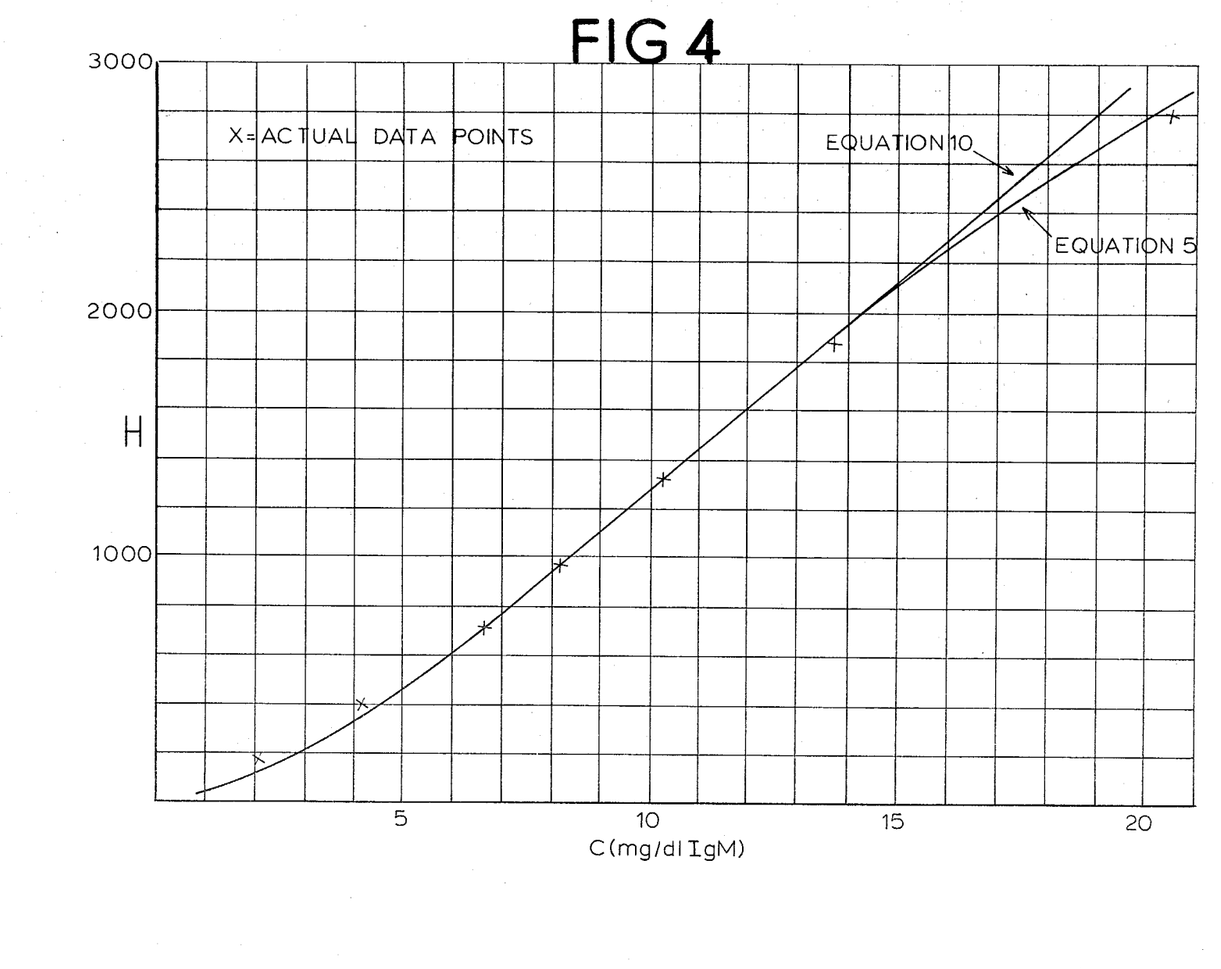
FIG. 4 is a graph of the fit of curves according to the present invention against actual data points for a human immunoglobulin M (IgM) antigen/antibody reaction.
Figure 5:
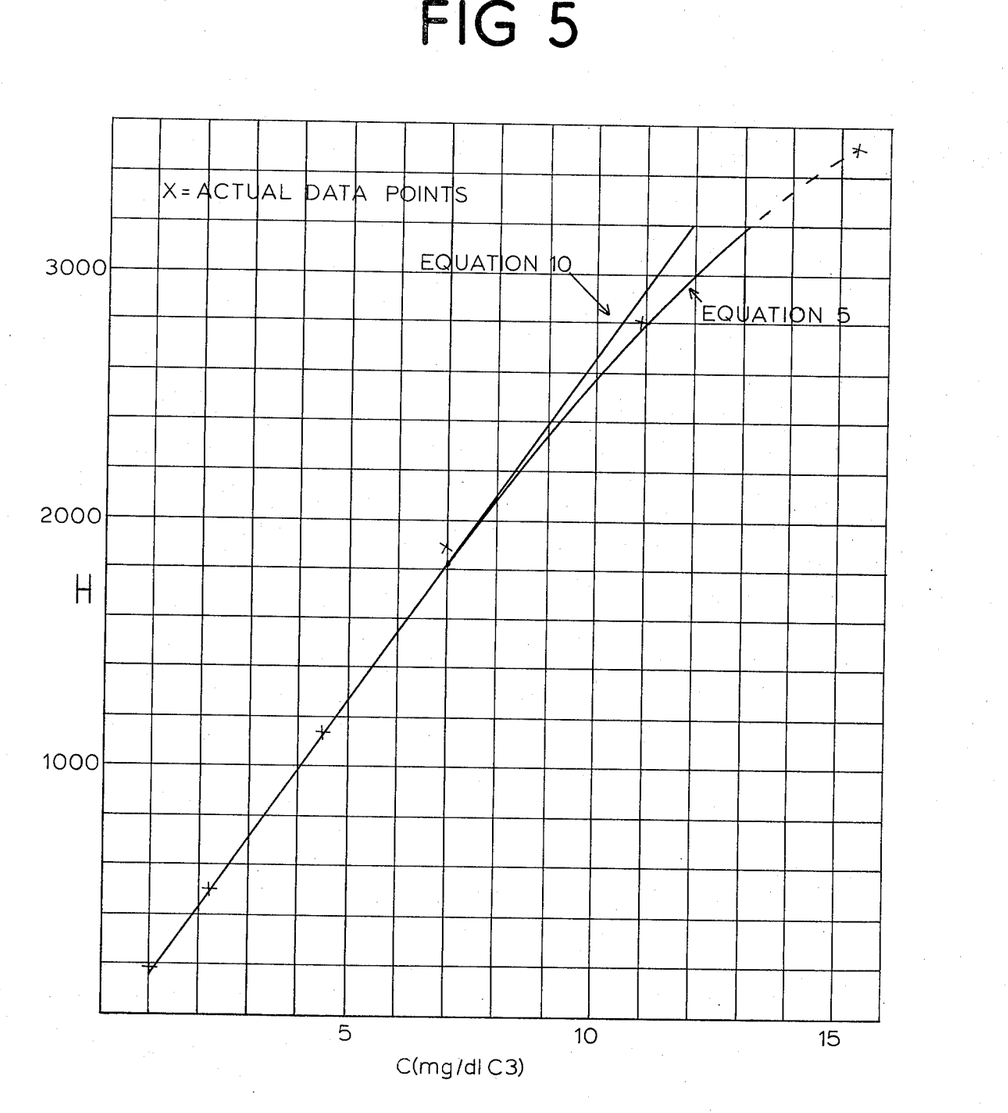
FIG. 5 is a graph of the fit of curves according to the present invention against actual data points for a third component of human complement (C'3) antigen/antibody reaction.
Figure 6:
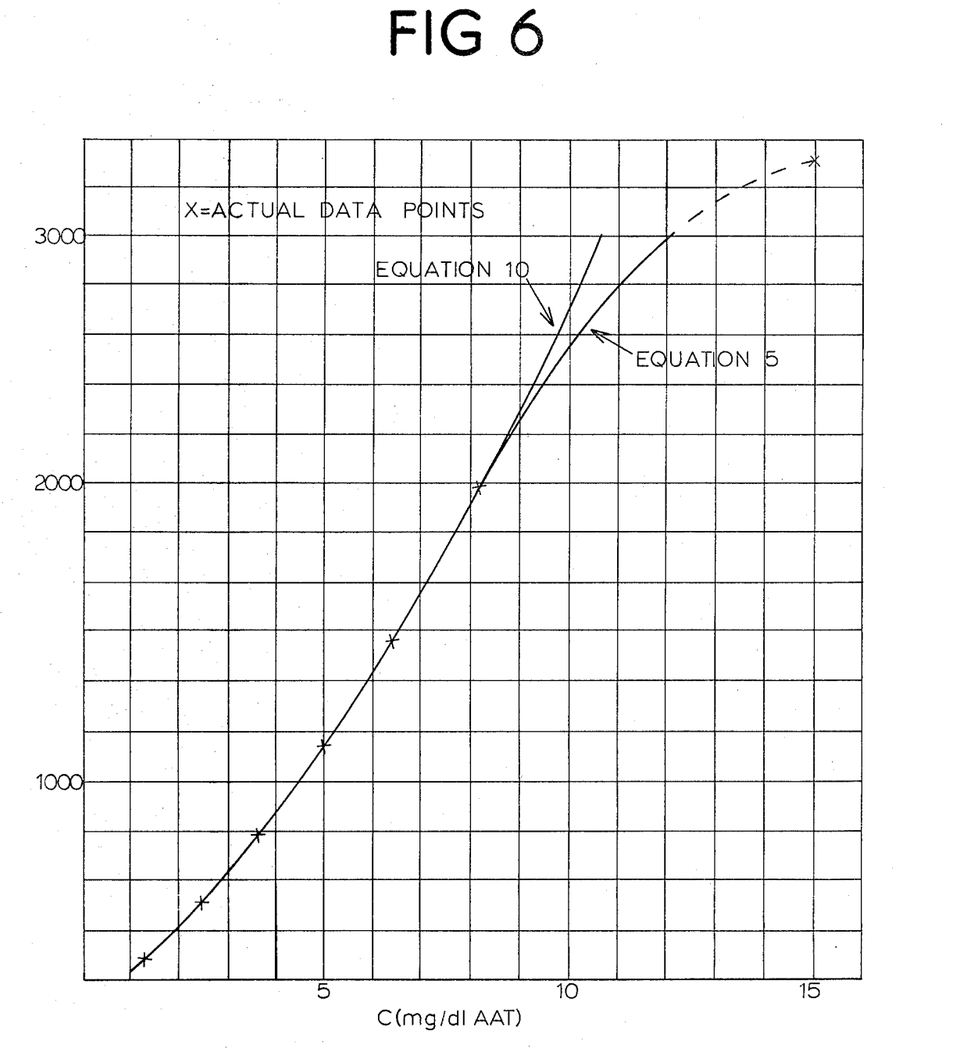
FIG. 6 is a graph of the fit of curves according to the present invention against actual data points for a human α-1-antitrypsin (AAT) antigen/antibody reaction.

Further, in the rate nephelometric method of monitoring immunochemical reactions, the curve of peak rate (H) plotted as a function of the antigen concentration (C) is both nonlinear and passes through a maximum as shown in FIG. 1. This means that the same observed peak rate can be indicative of two different values of antigen concentration.

An objective of the present invention is to rapidly obtain single valued meaningful quantitative antigen concentration information from the nonlinear but monotonically increasing portion of the H v. C curve in the antibody excess region normally used for antigen measurement. Note, however, that the process can be inverted for antibody measurement, using a fixed level of antigen to measure antibody in the antigen-excess portion of the curve.

In realizing the foregoing objective, it has been found possible to obtain a good mathematical approximation to the antibody excess portion of the H v. C response curve with a cubic equation of the particular form:

$$H = \frac{MEC^2(1 - AC)}{1 + (E - A)C} \quad (1)$$

where: M, E, and A are constants which will be discussed in detail hereinafter.

This equation results from considering the response curve of FIG. 1 to be made up of two parts, an ascending parabola $H_1$ at low concentration, and a descending parabola $H_2$ at high concentration of antigen. The low concentration portion of the curve is fit approximately by the expression:

$$H_1 = MEC^2 \quad (2)$$

which is a parabola having its vertex at the origin, while the higher concentration portion is fit approximately by:

$$H_2 = MC(1 - AC), \quad (3)$$

which is a parabola passing through the origin and having its maximum at $C = \frac{1}{2}A$.

Each of these terms may be regarded as representing a rate limiting step in a generally second-order interaction between antigen and antibody molecules. At low concentration, the $H_1$ expression is rate limiting. Possibly this is because at low antigen concentration the build-up of light scattering centers formed by the reaction is dependent on the probability of pairs of initial complexes coming together. The number of these complexes is proportional to the antigen concentration, when the antibody is present in vast excess over antigen. At higher concentration the rate becomes simply proportional to the antigen concentration, there being an essentially fixed excess of antibody. At still higher concentration, the available antibody is reduced by that already bound to antigen, so the product of antibody and antigen concentrations involves a subtractive term dependent on antigen level.

The foregoing may be more clearly understood by reference to an electrical analog of the chemistries involved. For example, if H represents a flow of "chemical current" i.e., reaction taking place—it can be regarded as inversely proportional to the resistance to chemical reaction. In the manner of an electrical circuit, such a resistance can be considered to be made up of two parts, proportional to the reciprocals of $H_1$ and $H_2$, respectively, acting in series. The "chemical resistance" equation then is:

$$\frac{1}{H} = \frac{1}{H_1} + \frac{1}{H_2} = \frac{1}{MEC^2} + \frac{1}{MC(1 - AC)} \quad (4)$$

or, solving for H:

$$H = \frac{MEC^2(1 - AC)}{1 + (E - A)C} \quad (5)$$

The constant A is inversely related to the titer of the antiserum. The constant E, which determines the initial rising parabolic portion, or "toe," of the H v. C curve, is related to avidity. The higher the value of E, the lower the concentration at which the $H_1$ term ceases to play a role, because its "chemical resistance", $1/H_1$, approaches zero. The constant M is system dependent and includes both chemical ($M_1$) and instrumental ($M_2$) contributions with:

$$M = M_1 M_2 \quad (6)$$

so that:

$$ME = M_1 E M_2 \quad (7)$$

where $M_1 E$ may be considered to be the "chemical gain" term and includes both the avidity-dependent contribution, E, and the factor $M_1$ which determines the amount of scatter signal at kinetic equivalence. $M_1$ is approximately proportional to the square of the titer of the antibody, since the rate at kinetic equivalence is proportional to the product of the antigen and antibody concentrations. $M_1$ also is proportional to the number of antibody sites per unit weight of antigen. The factor $M_2$ allows for instrumental scaling of the peak rate signal to a desired level, and thus constitutes the "instrumental gain" term. The actual determination of these constants will be discussed in greater detail hereinafter.

If the constants E and A are known for a particular reaction system (which is the usual case as will be seen later), the constant M can be determined from equation (5) by a single point calibration reaction conducted at a known concentration C by measuring the actual peak rate H achieved. Values of C can then be calculated for unknown samples from measured values of H using the now known constants M, E, and A and employing, for example, an iterative method of solving the cubic equation (5) for C.

Equation (5) has been found to fit most experimental response curves up to the kinetic equivalence point (H, $C_{ek}$ on FIG. 1). However, studies in the laboratories of the assignee hereof have shown that deviations can be observed in the response to the same concentration levels of the same antigen in different samples beyond about 80% of the antigen concentration, $C_{ek}$, at the kinetic equivalence point.

A simplification of equation (5) is followed well by experimental data for all analytes studied up to 50% of $C_{ek}$. This equation is derived similarly to equation (5), replacing $H_2$ in equation (3) by $H_3$, where:

$$H_3 = MC \tag{8}$$

then:

$$\frac{1}{H} = \frac{1}{H_1} + \frac{1}{H_3} = \frac{1}{MEC^2} + \frac{1}{MC} \tag{9}$$

or:

$$H = MEC^2/1 + EC \tag{10}$$

Where M and E have meanings similar to those in equation (5). Note that the A term is now absent and that equation (10) is a quadratic instead of a cubic. This simplifies the calculation of concentrations from peak rate data once the constants E and M are known.

While the simple operation (10) is easier to solve than equation (5), in practice it may prove desirable to use sufficient electronic filtering of the rate signal in the analysis apparatus to produce some attenuation of higher H values. This may lead to an earlier roll-off of the H v. C curve than would otherwise be observed. In such case, it then becomes preferable to use the cubic equation (5) to best fit the data, even over the more limited concentration range (less than 80% of $C_{ek}$) for which different samples have been found to exhibit similar behavior.

The fit of both equations (5) and (10) to data on the immunoglobulins G, A, and M (IgG, IgA, IgM, respectively) and on the third component of complement (C'3) and α-1-antitrypsin (AAT) is shown in FIGS. 2-6. It can be seen that the cubic equation (5) fits the experimental data over a significantly wider concentration range than does the quadratic equation (10).

It should also be noted that the cubic equation (5) reduces to the quadratic equation (10) if A=0, so a single format according to equation (5) can be used for either purpose, as desired. Furthermore, if $E >> 1/C$, even for the lowest C covered in the working range, equation (5) reduces to the form of equation (3), i.e., $$H = MC(1 - AC) \tag{11}$$

Then, if A=0, it reduces further to a simple straight line through the origin, $$H = MC \tag{12}$$

Thus, through proper selection of the constants, equation (5) can be made to reduce to either of two forms of quadratic equations (equations (10) or (11)), or to a linear (equation (12)), and is thus sufficiently flexible to cover a wide range of response characteristics.

The technique of assigning values to the constituents will be described and then applied to a specific example following the general discussion. A series of known concentrations (C) of antigen, covering the desired measuring range, is prepared by making a set of careful dilutions of a serum specimen containing a known level of the antigen assigned by accepted procedures. The peak height (H) is assigned for each concentration (C) as the mean of a set of rate nephelometric determinations performed at that concentration level, providing a set of known (H, C) data points. Equation (1) is rearranged into the following forms:

$$H = C^2 \cdot ME + C^3(-MEA) + HC(-(E-A)) \tag{13}$$

$$H/C = C \cdot ME + C^2(-MEA) + H(-(E-A)) \tag{14}$$

$$H/C^2 = 1 \cdot ME + C(-MEA) + (H/C)(-(E-A)) \tag{15}$$

Each of equations (13), (14), and (15) is seen to provide a linear equation in three unknowns (ME), (−MEA), and (−(E−A)), respectively) for each data point (H, C). For the set of (H, C) data points, then, each of the equations (13), (14), and (15) becomes a set of simultaneous linear equations in the above three unknowns. The set of equations can be solved for the above unknowns, and in turn employed to furnish the individual values of the constants M, E, and A, as desired.

The sets of simultaneous linear equations from (13), (14), and (15) are conveniently written in matrix form as $$\begin{pmatrix} H_1 \\ H_2 \\ H_3 \\ \cdot \\ \cdot \\ H_n \end{pmatrix} = \begin{pmatrix} C_1^2 & C_1^3 & H_1 C_1 \\ C_2^2 & C_2^3 & H_2 C_2 \\ C_3^2 & C_3^3 & H_3 C_3 \\ \cdot & \cdot & \cdot \\ \cdot & \cdot & \cdot \\ C_n^2 & C_n^3 & H_n C_n \end{pmatrix} \begin{pmatrix} ME \\ -MEA \\ -(E-A) \end{pmatrix} \tag{13A}$$

$$\begin{pmatrix} H_1/C_1 \\ H_2/C_2 \\ \cdot \\ \cdot \\ H_n/C_n \end{pmatrix} = \begin{pmatrix} C_1 & C_1^2 & H_1 \\ C_2 & C_2^2 & H_2 \\ \cdot & \cdot & \cdot \\ \cdot & \cdot & \cdot \\ C_n & C_n^2 & H_n \end{pmatrix} \begin{pmatrix} ME \\ -MEA \\ -(E-A) \end{pmatrix} \tag{14A}$$

$$\begin{pmatrix} H_1/C_1^2 \\ H_2/C_2^2 \\ \cdot \\ \cdot \\ H_n/C_n^2 \end{pmatrix} = \begin{pmatrix} 1 & C_1 & H_1/C_1 \\ 1 & C_2 & H_2/C_2 \\ \cdot & \cdot & \cdot \\ \cdot & \cdot & \cdot \\ 1 & C_n & H_n/C_n \end{pmatrix} \begin{pmatrix} ME \\ -MEA \\ -(E-A) \end{pmatrix} \tag{15A}$$

A known method of finding the best least squares solution to such sets of simultaneous linear equations is presented in Sternberg, J. C., Stillo, H. S., and Schwendeman, R. H., "Spectrophotometric Analysis of Multicomponent Systems Using Least Squares Method in Matrix Form, Ergosterol Irradiation System." Analytical Chem. 32, 84 (1960). The method is as follows. In the matrix equation:

$$A = B \cdot X \tag{16}$$

Where: A is an n×1 column matrix consisting of known—e.g., measured—parameters, B is an n×m matrix, also consisting of known parameters, and X is an m×1 column matrix containing as elements the m desired unknowns.

It is shown in the referenced article that the values of the unknowns minimizing the sum of squares of the errors in the elements of the A matrix (i.e., the sum of the squares of the differences between the "known," or experimentally determined, values of those elements and the values calculated using the solution set of assigned values of the unknowns), is given by the following procedure:

$$\tilde{B} \cdot A = \tilde{B} \cdot B \cdot X \tag{17}$$

which is rewritten as:

$$G = R \cdot X \tag{18}$$

where: $\tilde{B}$ (read B transpose) is the m×n matrix obtained by interchanging the rows and columns of matrix $B \cdot G = \tilde{B} \cdot A$ is an m×1 column matrix and $R = \tilde{B} \cdot B$ is a square m×m matrix, which in general will have an inverse, $R^{-1}$, such that:

$$R^{-1} \cdot R = 1 \quad (19)$$

where: 1 is the unit diagonal m×m matrix, having "ones" on all diagonal elements, and "zeros" on all off-diagonal elements.
Then:

$$R^{-1} \cdot G = R^{-1} \cdot R \cdot X = X \quad (20)$$

is the means of obtaining the X matrix, the elements of which are the desired unknowns.

In the case of matrix equations (13A), (14A) and (15A), m=3, and n≧3 corresponding to the number of data points (H, C) employed. This yields values of ME, $-$MEA, and $-(E-A)$, as $X_1$, $X_2$ and $X_3$, respectively, from which:

$$A = -(-MEA)/(ME) = -X_2/X_1; \quad (21)$$

$$E = A - (-(E-A)) = -(X_2/X_1) - X_3; \text{ and,} \quad (22)$$

$$M = (ME)/E = (X_1)/(-(X_2/X_1) - X_3). \quad (23)$$

Known prior art use of least squares methods for curve fitting would minimize the sum of the squares of the deviations of the dependent variable (H), and thus would utilize the equation sequence (13), (13A). Such an approach, however, treats absolute deviations at high H values equivalently to those at low H values, and can accept large percentage errors at low H values. Better overall curve fitting from the standpoint of relative error is obtained with equations (14), (14A) or equations (15), (15A). In any given case, the better fit of these two sets is used to provide the values of M, E, and A. We use as ultimate criteria of goodness of fit a measure we term the relative standard deviation in H defined by $$RSD \text{ in } H = 100 \sqrt{\frac{\Sigma((H_{calc} - H_{obs})^2/H_{obs}^2)}{N-1}} \%$$

The solution set of values of M, E, and A, from among the equation sequences (13), (13A), or (14), (14A), or (15), (15A), yielding the lowest RSD in H provides the assigned values of these constants. Using this approach, in practice, calculated curves typically fit experimental data within ±3% over the entire measuring range.

The set of constants, M, E, and A, characterize a particular lot of antiserum with respect to its response behavior in suitable analytical apparatus employing a rate nephelometric technique. A rate nephelometric instrumental system built by the assignee of this invention is designed to accept these constant values an input data, along with an assigned concentration value for a calibrator solution. The rate peak ($H_1$) obtained by actual analysis of the calibrator is compared to the value corresponding to solution of equation (1) for H at the assigned values of M, E, A, and the assigned value of C for the calibrator. The ratio of calculated to observed H values for the calibrator is used as a correction factor by which measured peak rates for subsequent samples are multiplied. The instrument is then calibrated, and thereafter can be made to display results directly as concentrations, rather than as peak rates.

In subsequent analysis on unknown samples, each measured peak rate is multiplied by the instrumental correction factor to provide a corrected peak rate, H', which is used in equation (1), along with the assigned M, E, and A values, to determine the concentration C. Equation (1) can be rewritten as:

$$C = \frac{(E-A)\left(\frac{H'}{1-AC}\right) + \sqrt{(E-A)^2\left(\frac{H'}{1-AC}\right)^2 + 4ME\left(\frac{H'}{1-AC}\right)}}{2ME} \quad (24)$$

and solved iteratively for C, with the nth iteration employing the (n−1)st value of C on the right hand side. Thus, $$C_n = \frac{(E-A)\left(\frac{H'}{1-AC_{n-1}}\right) + \sqrt{(E-A)^2\left(\frac{H'}{1-AC_{n-1}}\right)^2 + 4ME\left(\frac{H'}{1-AC_{n-1}}\right)}}{2ME} \quad (25)$$

is employed until $C_n - C_{n-1}$ is within a specified narrow limit. Obviously, other methods of solving the cubic equation (1) for C can be used. Despite the inherently nonlinear response characteristics of such systems, concentrations can be determined from measured peak heights on the basis of only single-point calibration through employing the semi-empirical equation (1) in a rate nephelometric system.

The foregoing method is illustrated in the following example. Although the example was specifically obtained for IgG, results similar in principle have been obtained with all other antigens studied.

EXAMPLE: Determination of the constants M, E, and A for a preparation of anti-human immunoglobulin G (IgG).

A calibrating serum was prepared having an IgG concentration value of 1800 mg/dl by the commercially available Automated Immuno-precipitation Method (Technicon Corp., Tarrytown, N.Y.) referenced against a World Health Organization reference serum. A source of dilutions of the calibrating serum in isotonic saline was prepared as follows: 1:108, 1:144, 1:180, 1:216, 1:432, 1:864, 1:1080. Introduction of 35 μl of each of the above dilutions into 500 μl of a buffered polyethylene glycol (PEG) solution was followed by introduction of 35 μl of a 1:8 dilution of the anti-IgG being evaluated. The resultant immuno-precipitin reactions were monitored by rate nephelometric apparatus and the peak rates (H) were determined for each concentration (C), giving the following results.

| Dilution | C mg/dl | H (Arbitrary Units) |
|---|---|---|
| 1:108 | 16.67 | 2697 |
| 1:144 | 12.50 | 2070 |
| 1:180 | 10 | 1710 |
| 1:216 | 8.33 | 1437 |
| 1:432 | 4.17 | 611 |
| 1:648 | 2.78 | 336 |
| 1:864 | 2.08 | 215 |
| 1:1080 | 1.67 | 151 |

Least squares solution of the simultaneous linear equation sets of the form (13A), (14A), and (15A) according to the matrix method of equations (16) through (20) furnished the following results: H solution (equations 13A)

$E = 0.288$, $A = 0.0187$, $m = 319$, RSD in $H = 2.67\%$
H/C Solution (equations 14A)

$E = 0.319$, $A = 0.0189$, $M = 316$, RSD in $H = 2.35\%$
H/C$^2$ solution (equations 15A)

$E = 0.296$, $A = 0.0210$, $M = 334$, RSD in $H = 1.71\%$
The "RSD in H" is an indication of how well the calculated curve fits to the experimental curve, and is found from the relationship $$RSD \text{ in } H = 100 \sqrt{\frac{\Sigma((H_{calc} - H_{obs})^2/H_{obs}^2)}{N - 1}} \%$$

where: $H_{calc}$ and $H_{obs}$ are the calculated and observed peak rates, respectively, and N is the number of data points entered (8 in the foregoing example).

M is essentially a scaling factor on H; thus, the value of M can be adjusted for any desired criterion. In this case, it has been adjusted to cause the calculated value of H to be 3200 when the concentration is 16.67 mg/dl (representing a 1:216 dilution of a 3600 mg/dl sample). This was arbitrarily selected as an overrange condition, with $H > 3200$ rejected in subsequent analyses as being beyond the accurate measuring range.

Samples are normally diluted 1:216 for IgG determination with the instrument system utilized in the foregoing example.

The "best set" of M, E, and A constants (334, 0.296, 0.0210) is entered, and a calibrator (e.g., at 1800 mg/dl IgG) introduced a the 1:216 dilution. The instrument automatically adjusts the peak rate reading to 1721 by the previously described technique (which corresponds to the calculated H for C of 1800÷216=8.3 mg/dl with the assigned M, E, and A values) and displays a calibrated reading of 1800 mg/dl. Subsequent unknown samples introduced at 1:216 dilution are run, the C values computed from the corrected observed H values using equation (1) with the assigned M, E, and A values, and the answer reported is the calculated C: 216. Samples falling outside the normal measuring range are run at 1:36 or 1:1296 dilution, with the C value obtained from equation (1) then multiplied by 36 or 1296, respectively, to provide the direct readout, all on the basis of calibration at the single point.

I claim:

1. For use with a nephelometric measuring system, a method of rate nephelometric immunochemical analysis in which an antigen is reacted with a reagent containing an antibody and the antigen concentration C is determined according to the formula $$H = \frac{MEC^2(1 - AC)}{1 + (E - A)C}$$

where A is an empirical constant inversely related to the titer of the antigen, E is an empirical constant related to avidity, M is an empirical constant determining the overall scaling and sensitivity of the measuring system, and H is the peak rate of change of a nephelometric signal produced by the antigen-antibody reagent reaction, said method comprising the steps of:

(1) calibrating the measuring system by the sub-steps of:
  (a) initiating a reaction between a known concentration of a single antigen sample (calibrator) and the antibody reagent to be used in unknown concentration sample analysis;
  (b) monitoring the rate of change with respect to time of the nephelometric signal produced by the calibrator antigen-antibody reaction to determine the peak rate H; and
  (c) solving the foregoing equation for M using the E and A constants of the reagent, the known C of the single calibrator antigen and the observed peak rate H; and (2) analyzing an unknown sample by the further sub-steps of:
  (d) initiating a reaction between an unknown concentration of antigen sample and the antibody reagent;
  (e) monitoring the rate of change with respect to time of the nephelometric signal produced by the unknown antigen-antibody reaction to determine the peak rate H; and
  (f) solving the foregoing equation for the unknown antigen concentration C from the value of H determined in step (e), the known values of E and A, and the value of M determined in step (c) from the single calibrator antigen-antibody reaction of step (a).

* * * * *